(12) United States Patent
Carlton et al.

(10) Patent No.: US 7,332,307 B2
(45) Date of Patent: Feb. 19, 2008

(54) ANTIBACTERIAL THERAPY WITH BACTERIOPHAGE PHYSICO-CHEMICALLY ALTERED BY PEGYLATION TO DELAY INACTIVATION BY THE HOST DEFENSE SYSTEM

(75) Inventors: Richard M. Carlton, Port Washington, NY (US); Carl R. Merril, Rockville, MD (US); Sankar L. Adhya, Gaithersburg, MD (US)

(73) Assignees: The United States of America as represented by the Department of Health and Human Services, Washington, DC (US); Exponential Biotherapies, Inc., New York, NY (US)

( * ) Notice: Subject to any disclaimer, the term of this patent is extended or adjusted under 35 U.S.C. 154(b) by 205 days.

(21) Appl. No.: 10/659,698

(22) Filed: Sep. 11, 2003

(65) Prior Publication Data

US 2004/0161431 A1 Aug. 19, 2004

Related U.S. Application Data

(63) Continuation of application No. 09/865,717, filed on May 29, 2001, now abandoned, which is a continuation of application No. 08/944,512, filed on Oct. 6, 1997, now abandoned, which is a continuation of application No. 08/222,952, filed on Apr. 5, 1994, now abandoned.

(51) Int. Cl.
*C12N 15/64* (2006.01)
(52) U.S. Cl. ................................ 435/91.4
(58) Field of Classification Search ............ 435/235.1, 435/238, 138; 424/184.1
See application file for complete search history.

(56) References Cited

U.S. PATENT DOCUMENTS

| | | | |
|---|---|---|---|
| 4,332,897 A | 6/1982 | Nakano et al. | |
| 4,375,734 A | 3/1983 | Kozloff et al. | |
| 4,797,363 A | 1/1989 | Teodorescu et al. | |
| 4,865,979 A | 9/1989 | Nakano et al. | |
| 4,946,778 A | 8/1990 | Ladner et al. | |
| 5,132,221 A | 7/1992 | Ward et al. | |
| 5,168,037 A | 12/1992 | Entis et al. | |
| 5,284,934 A | 2/1994 | Allen, Jr. | |
| 5,344,822 A | 9/1994 | Levine et al. | |
| 5,660,812 A | 8/1997 | Merril et al. | |
| 5,688,501 A | 11/1997 | Merril et al. | |
| 5,766,892 A | 6/1998 | Merril et al. | |
| 5,811,093 A | 9/1998 | Merril et al. | |
| 2001/0026795 A1 | 10/2001 | Merril et al. | |
| 2001/0043917 A1 | 11/2001 | Merril et al. | |
| 2003/0026785 A1 | 2/2003 | Merril et al. | |
| 2004/0161411 A1 | 8/2004 | Merril et al. | |
| 2005/0063957 A1 | 3/2005 | Merril et al. | |

FOREIGN PATENT DOCUMENTS

| | | |
|---|---|---|
| WO | WO 95/27043 A1 | 10/1995 |
| WO | WO 97/39118 A1 | 10/1997 |

OTHER PUBLICATIONS

Nucci et al. "The therapeutic value of poly(ethylene glycol)-modified proteins", Advanced Drug Delivery Reviews, vol. 6, Issue 2, Mar.-Apr. 1991, pp. 133-151. Abstract only.*
Merril CR, et al. Long-circulating bacteriophage as antibacterial agents. Proc. Natl. Acad. Sci. USA vol. 93, pp. 3188-3192, Apr. 1996.*
Nucci ML, et al. The therapeutic value of poly(ethylene glycol)-modified proteins. Advanced Drug Delivery Reviews, 6 (1991) 133-151.*
O'Riordan CR et al. "PEGylation of Adenovirus Retention of Infectivity and Protection from Neutralizing Antibody in Vitro and in Vivo". Human Gene Therapy 10:1349-1358 (May 20, 1999).*
DeHaard, et al. Llama Antibodies agains a Lactococcal Protein Located at the Tip of the Phage Tail Prevent Phage Infection. 2005 J Bacteriol. 187(13):4531-4541.*
O'Riordan CR et al. "PEGylation of Adenovirus with Retention of Infectivity and Protection from Neutralizing Antibody in Vitro and in Vivo". Human Gene Therapy 10:1349-1358 (May 20, 1999).*
Geier, et al. Fate of Bacteriophage Lambda in Non-Immune, Germ-Free Mice. Nature. 1973; 246:221-222.*
Angel, M.F. et al. 1987 "Beneficial effects of staphage lysate in the treatment of chronic recurrent hidradenitis suppurativa," *Surgical Forum* 38:111-112.
Audesirk, G. et al. 1986 *Biology Life on Earth*, Macmillan Publishing Company, N.Y. pp. 202-203.
Bendinelli, M. et al. 1988 "Disruption of Phagosomal Membrane by the Virulent H37Rv Strain of *M. tuberculosis*" in: *Mycobacterium tuberculosis: Interactions With the Immune System* (Infectious Agents and Pathogenesis), Herman Friedman (Editor), Plenum Press, pp. 311-313.
Berchieri, A. Jr. et al. 1991 "The activity in the chicken alimentary tract of bacteriophages lytic for *Salmonella typhimurium*," *Res. Microbiol.* 142:541-549.

(Continued)

*Primary Examiner*—Mary E. Mosher
*Assistant Examiner*—Stuart W. Snyder
(74) *Attorney, Agent, or Firm*—Knobbe, Martens, Olson & Bear, LLP

(57) ABSTRACT

The present invention is directed to bacteriophage therapy, using methods which enable the bacteriophage to delay inactivation by any and all parts of the host defense system (HDS) against foreign objects. The HDS normally reduces the number of bacteriophage in an animal, which decreases the efficiency of the bacteriophage in killing the host bacteria present during an infection. Disclosed is a method of producing bacteriophage modified for anti-HDS purposes by physico-chemical alteration of the bacteriophage surface proteins, so that the altered bacteriophage remain active in the body for longer periods of time than the unmodified bacteriophage.

2 Claims, No Drawings

OTHER PUBLICATIONS

Bogovazova, G.G. et al. 1992 "Immunobiological properties and therapeutic effectiveness of *Klebsiella* bacteriophages preparations," *Zh. Mikrobiol. Epidemiol. Immunobiol.* 3:30-33.

Cislo, M. et al. 1987 "Bacteriophage treatment of suppurative skin infections." *Arch Immunol Ther Exp (Warsz)*, 35:175-183.

Engelstad, M. et al. 1992 "A constitutively expressed vaccinia gene encodes a 42-kDa glycoprotein related to complement control factors that forms part of the extracellular virus envelope." *Virology* 188:801-810.

Frank, M.M. et al. 1992 "The Mechanism by which microorganisms avoid complement attack," *Curr. Opin. Immunol.* 4:14-19.

Geier, M.R. et al. 1973 "Fate of bacteriophage Lamda in non-immune germ-free mice," *Nature* 246:221-222.

Gherna, R., et al. 1992 *American Type Culture Collection Catalogue of Bacteria and Phages*, Eighteenth edition, pp. 402-409.

Hidaka, Y. et al. 1991 "Glycoprotein C of herpes simplex virus type 1 is essential for the virus to evade antibody-independent complement-mediated virus inactivation and lysis of virus-infected cells" *J. Gen. Virol.* 72:915-921.

Isaacs, S.N. et al. 1992 "Characterization of a vaccinia virus-encoded 42-kilodalton class I membrane glycoprotein component of the extracellular virus envelope" *J. Virol.* 66:7217-7224.

Isaacs, S.N. et al., 1992 "Vaccinia virus complement-control protein prevents antibody-dependent complement-enhanced neutralization of infectivity and contributes to virulence" *PNAS USA* 89:628-632.

Jackson, R.J. et al. 2001 "Expression of mouse interleukin-4 by a recombinant ectromelia virus suppresses cytolytic lymphocyte responses and overcomes genetic resistance to mousepox," *J. Virol.* 75:1205-1210.

Kress, D.W. et al. 1980 "A preliminary report on the use of staphage lysate for treatment of hidradenitis suppurativa," *Ann. Plastic Surgery* 6:393-395.

Kucharewicz-Krukowska, A. et al. 1987 "Immunogenic effect of bacteriophage in patients subjected to phage therapy." *Arch Immunol Ther Exp (Warsz).* 35:553-561.

Lambris, J.D. et al. 1993 "Use of synthetic peptides in exploring and modifying complement reactivities." In *Activators and inhibitors of complement activation*. R.B. Sim, editor. Kluwer Academic Press, Lancaster. pp. 201-232.

Merril, C.R. et al. (1996) "Long-circulating bacteriophage as anti-bacterial agents," *PNAS USA* 93:3188-3192.

Montefiori, D.C. et al. 1994 "Complement control proteins, CD46, CD55, and CD59, as common surface constituents of human and simian immunodeficiency viruses and possible targets for vaccine protection." *Virology*, 205:82-92.

Peake, P. et al. 1990 "Peptide inhibitors of C3 breakdown." *Clin. Exp. Immunol.* 79:454-458.

Peremitina, L.D. et al. 1981 "[Experience in the therapeutic use of bacteriophage preparations in suppurative surgical infections]" *Zh. Mikrobiol. Epidemiol. Immunobiol.* 9:109-110.

Roitt I.M. 1991 *Essential Immunology*, Seventh Edition, Blackwell Scientific Publications, pp. 110-113.

Rother, R.P. et al. 1995 "Protection of retroviral vector particles in human blood through complement inhibition." *Human Gene Therapy* 6:429-435.

Salmon, G.G. Jr. et al. 1963 "Staphage lysate therapy in chronic staphylccoccal infections," *J. Med. Soc. N. J.* 60:188-193.

Schasteen, C.S. et al., 1988 "Synthetic peptide inhibitors of complement serine proteases—II. Effects on hemolytic activity and production of C3a and C4a." *Molec. Immunol.* 25:1269-1275.

Slopek, S. et al. 1983 "Results of bacteriophage treatment of suppurative bacterial infections. I. General evauation of the results." *Arch Immunol Ther Exp (Warsz)* 31:267-291.

Slopek, S. et al. 1983 "Results of bacteriophage treatment of suppurative bacterial infections. II. Detailed evaluation of the results." *Arch Immunol Ther Exp (Warsz)* 31:293-297.

Slopek, S. et al. 1984 "Results of bacteriophage treatment of suppurative bacterial infections. III. Detailed evaluation of the results obtained in further 150 cases." *Arch Immunol Ther Exp (Warsz)* 32:317-335.

Slopek, S. et al. 1985 "Results of bacteriophage treatment of suppurative bacterial infections. IV. Evaluation of the results obtained in 370 cases." *Arch Immunol Ther Exp (Warsz)* 33:219-240.

Slopek, S. et al. 1985 "Results of bacteriophage treatment of suppurative bacterial infections. VI. Analysis of treatment of suppurative staphylococcal infections," *Arch Immunol Ther Exp (Warsz)* 33:261-273.

Smith, H.W. et al. 1982 "Successful treatment of experimental *Escherichia coli* infections in mice using phage: its general superiority over antibiotics," *J. Gen. Microbiol.* 128:307-318.

Smith, H.W. et al. 1983 "Effectiveness of phages in treating experimental *Escherichia coli* diarrhea in calves, piglets and lambs," *J. Gen. Microbiol.* 129:2659-2675.

Smith, H.W. et al. 1987 "The control of experimental *Escherichia coli* diarrhea in calves by means of bacteriophages," *J. Gen. Microbiol.* 133:1111-1126.

Soothill, J.S. 1992 "Treatment of experimental infections of mice with bacteriophages," *J. Med. Microbiol.* 37:258-261.

Stent, G. 1963 "The Twort-D'Herelle Phenomenon," in: *Molecular Biology of Bacterial Viruses*, W.H. Freeman and Co., San Francisco and London, Chapter 1, pp. 1-21.

Vymola, F. et al. 1974 "*Staphylococcal osteomyelitis*" *Ann. N Y Acad. Sci.* 236:508-514.

U.S. Appl. No. 08/222,952, filed Apr. 5, 1994 to Carlton et al.
U.S. Appl. No. 08/222,956, filed Apr. 5, 1994 to Merril et al.
U.S. Appl. No. 08/454,415, filed May 30, 1995 to Merril et al.
U.S. Appl. No. 08/454,417, filed May 30, 1995 to Merril et al.
U.S. Appl. No. 08/795,541, filed Feb. 6, 1997 to Merril et al.
U.S. Appl. No. 08/811,344, filed Mar. 4, 1997 to Merril et al.
U.S. Appl. No. 08/944,512, filed Oct. 6, 1997 to Carlton et al.
U.S. Appl. No. 09/865,717, filed May 29, 2001 to Carlton et al.

Nucci et al., "The therapeutic value of poly(ethylene glycol)-modified proteins," Advanced Drug Delivery Reviews 6: 133 (1991).

Chillon et al. "Adenovirus complexed with polyethylene glycol and cationic lipid is shielded from neutralizing antibodies in vitro." Gene Ther 5: 995 (1998).

O'Riordan et al. "PEGylation of Adenovirus with Retention of Infectivity and Protection from Neutralizing Antibody in Vitro and in Vivo." Hum Gene Ther 10: 1349 (May 1999).

Romanczuk et al. "Modification of an Adenoviral Vector with Biologically Selected Peptides: A Novel Strategy for Gene Delivery to Cells of Choice." Hum Gene Ther 10: 2615 (Nov. 1999).

Delgado et al. "Coupling of Poly(ethylene glycol) to Albumin under Very Mild Conditions by Activation with Tresyl Chloride: Characterization of the Conjugate by Partitioning in Aqueous Two-Phase Systems." Biotechnol Appl Biochem 12: 119 (1990).

* cited by examiner

ANTIBACTERIAL THERAPY WITH BACTERIOPHAGE PHYSICO-CHEMICALLY ALTERED BY PEGYLATION TO DELAY INACTIVATION BY THE HOST DEFENSE SYSTEM

FIELD OF THE INVENTION

The present invention relates to a method of delaying the inactivation of bacteriophages by an animal's host defense system (HDS). One method of delaying inactivation is the use of novel bacteriophages whose genomes have been modified. The modification of bacteriophage genomes for the purpose of delaying inactivation is described in U.S. patent application Ser. No. 08/222,954 entitled "Antibacterial Therapy with Bacteriophage Genotypically Modified to Delay Inactivation by the Host Defense System", filed on Apr. 5, 1994, the disclosure of which is herein incorporated by reference into the present specification. The present invention is directed to making a phenotypic change by attaching a polymer to phage surface proteins (i.e. physico-chemically altering the bacteriophage). Such polymers block or mask the phage antigenic sites from interactions with the HDS. This masking enables the altered bacteriophage to remain in the circulation and in the tissues longer than the unmodified phage. Thus, the altered bacteriophage is more effective at treating (or assisting in the treatment of) a bacterial infection, in a human or other animal.

The present invention is also directed to specific methods of using the physico-chemically altered bacteriophage (whether wild-type or genomically-modified) for treating infectious bacterial diseases. The route of administration can be by any means including for example, delivering the altered phage by aerosol to the lungs.

BACKGROUND OF THE INVENTION

In the 1920s, shortly after the discovery of bacterial viruses (bacteriophages), the medical community began to extensively pursue the treatment of bacterial diseases with bacteriophage therapy. The idea of using phage as a therapy for infectious bacterial diseases was first proposed by d'Herelle in 1918, as a logical application of the bacteriophages' known ability to invade and destroy bacteria. Although early reports of bacteriophage therapy were somewhat favorable, with continued clinical usage it became clear that this form of therapy was inconsistent and unpredictable in its results. Disappointment with phage as a means of therapy grew, because the great potential of these viruses to kill bacteria in vitro was not realized in vivo. This led to a decline in attempts to develop clinical usage of phage therapy, and that decline accelerated once antibiotics began to be introduced in the 1940s and 50s. From the 1960s to the present, some researchers who adopted certain bacteriophages as a laboratory tool and founded the field of molecular biology have speculated as to why phage therapy failed.

Despite the general failure of phage as therapy, isolated groups of physicians have continued to try to use these agents to treat infectious diseases. Many of these efforts have been concentrated in Russia and India, where the high costs of and lack of availability of antibiotics continues to stimulate a search for alternative therapies. See for example Vogovazova et al., "Effectiveness of *Klebsiella pneumoniae* Bacteriophage in the Treatment of Experimental *Klebsiella* Infection", *Zhurnal Mikrobiologii, Epidemiologii Immunobiologii*, pp. 5-8 (April, 1991); and Vogovazova et al., "Immunological Properties and Therapeutic Effectiveness of Preparations of *Klebsiella* Bacteriophages", *Zhurnal Mikrobiologii, Epidemiologii Immunobiologii*, pp. 30-33 (March, 1992)]. These articles are similar to most of the studies of phage therapy, including the first reports by d'Herelle, in that they lack many of the controls required by researchers who investigate anti-infectious therapies. In addition, these studies often have little or no quantification of clinical results. For example, in the second of the two Russian articles cited above, the Results section concerning *Klebsiella* phage therapy states that "Its use was effective in . . . ozena (38 patients), suppuration of the nasal sinus (5 patients) and of the middle ear (4 patients) . . . In all cases a positive clinical effect was achieved without side effects from the administration of the preparation". Unfortunately, there were no placebo controls or antibiotic controls, and no criteria were given for "improvement".

Another clinical use of phage that was developed in the 1950s and is currently still employed albeit to a limited extent, is the use of phage lysate, specifically staphphage lysate (SPL). The researchers in this field claim that a nonspecific, cell-mediated immune response to staph endotoxin is an integral and essential part of the claimed efficacy of the SPL. [See, eg., Esber et al., J. Immunopharmacol., Vol. 3, No. 1, pp. 79-92 (1981); Aoki et al., Augmenting Agents in Cancer Therapy (Raven, N.Y.), pp. 101-112 (1981); and Mudd et al., Ann. NY Acad. Sci., Vol. 236, pp. 244-251 (1974).] In this treatment, it seems that the purpose of using the phage is to lyse the bacteria specifically to obtain bacterial antigens, in a manner that those authors find preferential to lysing by sonication or other physical/chemical means. Here again, some difficulties arise in assessing these reports in the literature, because, in general, there are no placebo controls and no standard antibiotic controls against which to measure the reported efficacy of the SPL. More significantly, there is no suggestion in these articles to use phage per se in the treatment of bacterial diseases. Moreover, the articles do not suggest that phage should be modified in any manner that would delay the capture/sequestration of phage by the host defense system.

Since many patients will recover spontaneously from infections, studies must have carefully designed controls and explicit criteria to confirm that a new agent is effective. The lack of quantification and of controls in most of the phage reports from d'Herelle on makes it difficult if not impossible to determine if the phage therapies have had any beneficial effect.

As there are numerous reports of attempts at phage therapy, one would assume that had it been effective, it would have flourished in the period before antibiotics were introduced. But phage therapy has been virtually abandoned, except for the isolated pockets mentioned above.

As noted above, some of the founders of molecular biology who pioneered the use of specific phages to investigate the molecular basis of life processes have speculated as to why phage therapy was not effective. For example, G. Stent in his book *Molecular Biology of Bacterial Viruses*, WH Freeman & Co. (1963) pp. 8-9, stated the following:

"Just why bacteriophages, so virulent in their antibiotic action in vitro, proved to be so impotent in vivo, has never been adequately explained. Possibly the immediate antibody response of the patient against the phage protein upon hypodermic injection, the sensitivity of the phage to inactivation by gastric juices upon oral administration, and the facility with which bacteria acquire immunity or sport resistance against phage, all militated against the success of phage therapy."

In 1973, Dr. Carl Merril discovered along with his coworkers that phage lambda, administered by various routes (per os, IV, IM, IP) to germ-free, non-immune mice, was cleared out of the blood stream very rapidly by the organs of the reticulo-endothelial system, such as the spleen, liver and bone marrow. [See Geier. Trigg and Merril, "Fate of Bacteriophage Lambda in Non-Immune, Germ-Free Mice", *Nature*, 246, pp. 221-222 (1973).] These observations led Dr. Merril and his co-workers to suggest (in that same *Nature* article cited above) overcoming the problem by flooding the body with colloidal particles, so that the reticulo-endothelial system would be so overwhelmed engulfing the particles that the phage might escape capture. Dr. Merril and his co-workers did not pursue that approach at the time as there was very little demand for an alternative antibacterial treatment such as phage therapy in the 1970s, given the numerous and efficacious antibiotics available.

Subsequently, however, numerous bacterial pathogens of great importance to mankind have become multidrug resistant (MDR), and these MDR strains have spread rapidly around the world. As a result, hundreds of thousands of people now die each year from infections that could have been successfully treated by antibiotics just 4-5 years ago. [See e.g. C. Kunin, "Resistance to Antimicrobial Drugs—A Worldwide Calamity", Annals of Internal Medicine, 1993; 118:557-561; and H. Neu, "The Crisis in Antibiotic Resistance", *Science* 257, 21 Aug. 1992, pp. 1064-73.] In the case of MDR tuberculosis, e.g., immunocompromised as well as non-immunocompromised patients in our era are dying within the first month or so after the onset of symptoms, despite the use of as many as 11 different antibiotics.

Medical authorities have described multidrug resistance not just for TB, but for a wide variety of other infections as well. Some infectious disease experts have termed this situation a "global crisis". A search is underway for alternative modes and novel mechanisms for treating these MDR bacterial infections.

Bacteriophage therapy offers one possible alternative treatment. Learning from the failure of bacteriophage therapy in the past, the present inventors have discovered effective ways to overcome the major obstacles that were the cause of that failure.

One object of the present invention is to develop a drug delivery vehicle wherein bacteriophages are protected by attaching to their surfaces a substance that can mask the phage surface antigens. This masking can be achieved by means such as, but not limited to, attaching substances in close proximity to the antigenic site, or attaching substances directly into the antigenic site, in either case, thereby blocking the host defense system's components from making contact with the antigenic site. The purpose of masking the antigenic site is to enable a bacteriophage to delay being inactivated by the host defense system.

Substances which can be used to mask phage surface antigens include a variety of polymers, both synthetic and natural, including but not limited to: polyethers, such as polyethylene glycol, polypropylene glycol, polypropylene oxide, polyvinylpyrrolidone, polyvinyl alcohol, polybutanediol, polysaccharides, hyaluronic acid, collagen, albumin, dextran, carboxymethylcellulose, and poly-D,L-amino acids.

Polyethylene glycol (PEG) is a well established immune system modifier already in clinical use, one of its major properties being its ability to protect the antigenic sites of proteins from interaction with the immune system.

PEG adducts are known in the art to prolong the circulating life of proteins that interact with the HDS. [See e.g. Nucci, M. L. et al., *The Therapeutic Value of Poly(ethylene glycol)-Modified Proteins*, Advanced Drug Delivery Reviews, 6, 1991, 133-151]. In this way, a shell of PEG molecules around one or more of the antigenic proteins of the phage will sterically hinder those proteins from interacting with complement, with immune cells, or with any other aspect of the HDS.

One example of the use of PEG to sterically prevent the interaction of the HDS with the antigens of a protein, is the drug ADAGEN™ (pegademase bovine). This PEG-modified protein is currently marketed for the treatment of severe combined immunodeficiency disease (SCID), a disease which is associated with adenosine deaminase deficiency. PEGylation of the enzyme slows its degradation and thereby renders it efficacious as a therapeutic. [See e.g. Hershfield, M. et al, Treatment of Adenosine Deaminase Deficiency with Polyethylene Glycol-Modified Adenosine Deaminase, New England Journal of Medicine, 316:589-596 Mar. 5, 1987.] One of the derivatives of PEG that is reported to have great stability, as well as high affinity and selectivity as a linker to antigens that are to be masked, is monomethoxypoly(ethylene glycol) (mPEG).

There are a number of methods known in the art to activate polymers so that they will bind with the target protein. The reagents to be used in the present invention, and known in the art for the activation of polymers for binding, include: trichloro-s-triazine (cyanuric chloride); carbonyldiimidazole; succinic anhydride; and succinimidyl carbonate. Succinimidyl carbonate is preferred for use in the present invention. The adduct targets on the protein include (but are not limited to): specific amino acid groups, sulfhydryl groups, and or other applicable moieties of the phage surface antigens that are to be masked.

The physico-chemical alteration of bacteriophage in the present invention allows a delay in their inactivation by the HDS, so that the phage are no longer prevented by the HDS from reaching and killing the target bacteria. The masking of the phage antigenic sites also decreases the tendency for the human or animal recipient of the phage therapy to form antibodies against the phage. As a result, the phage therapy remains useful for longer periods of time, and/or for more courses of treatment.

In the present invention, the adduct of the polymer with phage surface proteins is custom designed by methods known in the art, e.g. by: 1) varying the molecular weight of the polymer, 2) altering the reaction variables, for example: the concentrations of the reagents (such as the molecule used to activate the PEG reaction); the time course of the reaction (this changes the percentage of the amino acid groups of the phage surface antigen that become modified); the temperature; the pH; etc., 3) altering the type of PEG activator being used; and/or 4) altering the PEG derivative chosen for the reaction—one example among many being the bifunctional analog of SC-PEG known as poly(ethylene glycol)-bis-N-succinimidyl carbonate ("BSC-PEG"). These alterations provide a variety of physico-chemically altered bacteriophages, from which the ones demonstrating the best ability to delay inactivation by the HDS can be selected.

Given that the chemical substances linked to the bacteriophages cannot be genetically transmitted to progeny, it follows that the daughter phages will have no protection (by physico-chemical alteration) from the HDS. Nevertheless for each physico-chemically altered bacteriophage that does succeed in infecting a bacterium, on average a few hundred daughter phages are released within about a half hour (the actual number released and the time to burst depend on factors including the strain of bacteria and the strain of phage). Many of these daughter phage then have the opportunity to infect nearby bacteria, before the HDS has time to inactivate them. Therefore the rate at which the phage are multiplying is greater than the rate at which they are being taken out (by phagocytosis, complement fixation, or any other aspect of the host defense system), resulting in exponential growth in the number of phages at the site of an infection. Thus the physico-chemically altered phage of the present invention establish a "beachhead", wherein the succeeding "waves" of bacteriophage (the first "wave" being the parent generation of physico-chemically altered phage, and the following "waves" being the succeeding generations of unmodified daughter phages) combine to substantially eliminate the infectious bacteria.

While PEG and the other polymers listed above are examples of substances which can protect proteins from interaction with the HDS, there are many other suitable substances. Such substances are known to those skilled in the art and any of these substances can be used in the present invention.

Another object of the present invention is to develop a method for treating bacterial infectious diseases in an animal by administering to the animal, by an appropriate route of administration, an effective amount of the physico-chemically altered bacteriophage.

SUMMARY OF THE INVENTION

In the present invention, bacteriophages are physico-chemically altered to produce bacteriophages capable of delaying inactivation by any component of an animal's host defense system (HDS) against foreign bodies. The physico-chemical alteration can be by attachment of suitable polymers, or of any other suitable substance. The term "physico-chemical alteration" applies to all polymers that can physico-chemically modify a phage in such a way as to delay its inactivation by the HDS. These phage, referred to as "anti-HDS physico-chemically altered phage", are able to survive for longer periods of time in the circulation and in the tissues of an animal than the unmodified phage, thereby prolonging viability and making the phage more efficient at reaching and invading the bacteria at the site of an infection.

One embodiment of the present invention is the administration of the physico-chemically altered phage via aerosol to the lungs. This mode of administration is indicated in bacterial infections of the lungs, such as tuberculosis.

The administration of an anti-HDS modified phage will enable the animal recipient to efficaciously fight an infection with the corresponding bacterial pathogen. The phage therapy of this invention will therefore be useful either as an adjunct to standard anti-infective therapies, or as a standalone therapy.

The phages of the present invention can be administered by any route, such as oral, pulmonary (by aerosol or by other respiratory device for respiratory tract infections), nasal, IV, IP, per vagina, per rectum, intra-ocular, by lumbar puncture, intrathecal, and by burr hole or craniotomy if need be for direct insertion onto the meninges (e.g. in a heavily thickened and rapidly fatal tuberculous meningitis).

DETAILED DESCRIPTION OF THE INVENTION

One of the major obstacles to bacteriophage therapy is the fact that when phages are administered to animals, they are rapidly eliminated by the animal's HDS. That suggests that the phages are not viable in the animal's circulation or tissues for a long enough time to reach the site of infection and invade the bacteria. Thus, the object of the present invention is to physico-chemically alter the bacteriophages, so as to delay inactivation by the HDS. This will prolong phage viability in the body.

The attachment of a polymer to the bacteriophage increases its circulating life and reduces its immunogenicity and antigenicity. One example of such a polymer is PEG (polyethylene glycol). PEG is a linear, uncharged, flexible polymer available in a variety of molecular weights. In the present invention, the PEG strands are attached to the phage and sterically block the antigenic site from antibody attachment. Prior to PEGylating the bacteriophage, the tail proteins of the phages are protected from being PEGylated so as to protect those tail proteins from the steric hindrance that PEGylation would otherwise induce. The tail portion of the phage must be protected from PEGylation to ensure that it will adhere to the host bacteria so that it can inject its DNA into the bacteria. The steric hindrance caused by polymers (such as polyethylene glycol) is stated in the art as being the likely mechanism by which said polymers are able to protect protein antigenic sites from interacting with the immune system. [See e.g. Davis, F. F. et al. (1991) Reduction of immunogenicity and extension of circulation half-life of peptides and proteins. In: V. H. L. Lee (Ed.), Peptide and Protein Drug Delivery, Marcel Dekker, NY, pp. 831-864. ] However, the proteins of bacteriophage tails are in general the specific means by which bacteriophage adhere to and subsequently infect the host bacteria. Therefore any steric hindrance of the phage tail proteins themselves, which might be induced by the attachment of PEG or other polymers in the present invention, is to be avoided.

PEG has been approved by the Food and Drug Administration (FDA) as a vehicle or base for a number of pharmaceutical preparations, and has a low order of toxicity when administered orally and parenterally.

The term "host defense system" as used herein refers to all of the various structures and functions that help an animal to eliminate foreign bodies. These defenses include but are not limited to the formed cells of the immune system and the humoral components of the immune system, those humoral components including such substances as complement, lysozymes and beta-lysin. In addition, the organs of what has often been referred to as the "reticulo-endothelial system" (spleen, liver, bone marrow, lymph glands, etc.) also serve as part of the host defense system. In addition to all the phenomena cited just above which take place within this "reticulo-endothelial system", there has also been described a sequestering action wherein foreign materials (specifically including bacteriophage) are captured non-phagocytically and non-destructively in the spleen by what is known as the Schweigger-Seidel capillary sheaths [See e.g. Nagy, Z., Horrath, E., and Urban, Z., Nature New Biology, 242: p. 241 (1973).]

The phrase "substantially eliminate" as used regarding the present invention, indicates that the bacteria are reduced to a number which can then be completely (or at least sufficiently) eliminated by the animal's defense system, or by using conventional antibacterial therapies.

Enabling bacteriophages to delay inactivation by those host defense systems—whichever components of it may or may not be employed in any given case—would be likely to result in an increased in vivo killing of bacterial pathogens that are in the host range for those bacteriophages.

As used herein, the term "anti-HDS physico-chemically altered phage" is intended to cover not only those phages that have been modified by the attachment of various PEG derivatives, but also phages that have been modified by any of the numerous additional polymers known in the art. Such "physico-chemically altered" phages may be wild-type, or alternatively may have been previously modified by other procedures, such as genomic alterations (made by serial passage or by genetic engineering techniques). Further, a "physico-chemically altered" phage, as used herein, has a half-life within the animal that is at least 15% greater than the half-life of the original unmodified phage from which it was derived. Half-life refers to the point in time when, out of an initial IV dose (e.g. $1 \times 10^{12}$) of a given phage, half ($1 \times 10^6$) of them still remain in circulation, as determined by serial pfu experiments ("pfu" meaning plaque forming units, a convenient measure of how many phage are present in a given sample being assayed). A 15% longer half-life indicates a successful delay of inactivation by the HDS. In the case where a polymer is attached to a phage that is already able to delay inactivation by virtue of genotypic changes, then the additional modification of the present invention imparts an increase of at least an additional 15%, above and beyond the baseline extended half-life that has already been conferred by virtue of said genotypic changes.

Additional evidence that the HDS-evading phages do in fact remain viable for a longer period of time in the body is obtained by demonstrating not only the longer time that they remain in the circulation (see above), but also by the higher numbers of them that remain in the circulation at a given point in time. This slower rate of clearance can be demonstrated by the fact that e.g. ten minutes after the IV injection of $1 \times 10^{12}$ of the anti-HDS modified phage into a test animal, the number of the phages still in circulation (as measured by pfu assays) is at least 10% higher than the number of the corresponding unmodified phage still in circulation in the control animal, at that point in time.

The present invention can be applied across the spectrum of bacterial diseases, through attachment of suitable polymers to wild-type phage or to genotypically modified phage, so that anti-HDS modified phages are developed that are specific for each of the bacterial strains of interest. In that way, a full array of anti-HDS modified phages can be developed for virtually all the bacterial pathogens of man, his pets, livestock and zoo animals (whether mammal, avian, or pisciculture). Anti-HDS modified phage therapy will then be available:

1) as an adjunct to or as a replacement for those antibiotics and/or chemotherapeutic drugs that are no longer functioning in a bacteriostatic or bactericidal manner due to the development of multi-drug resistance;

2) as a treatment for those patients who are allergic to the antibiotics and/or chemotherapeutic drugs that would otherwise be indicated; and 3) as a treatment that has fewer side effects than many of the antibiotics and/or chemotherapeutic drugs that would otherwise be indicated for a given infection.

The second embodiment of the present invention is the development of methods to treat bacterial infections in animals through phage therapy with the anti-HDS physico-chemically altered bacteriophages. Hundreds of bacteriophages and the bacterial species they infect are known in the art. The present invention is not limited to a specific bacteriophage or a specific bacteria. Rather, the present invention can be utilized to develop anti-HDS physico-chemically altered bacteriophages which can be used to treat any and all infections caused by their host bacteria.

While it is contemplated that the present invention can be used to treat any bacterial infection in an animal, it is particularly contemplated that the methods described herein will be very useful as a therapy (adjunctive or stand-alone) in infections caused by drug-resistant bacteria. Experts report [See e.g. Gibbons, A., "Exploring New Strategies to Fight Drug-Resistant Microbes, Science, 21 Aug. 1993, pp. 1036-38.] that at the present time, the drug-resistant bacterial species and strains listed below represent the greatest threat to mankind:

1. All of the clinically important members of the family Enterobacteriaceae, most notably but not limited to the following:
a) All the clinically important strains of *Escherichia*, most notably *E. coli*. One among a number of possible wild-type phages against these particular pathogens that could be used as a starting point for the serial passage and/or the genetic engineering of the present invention would be ATCC phage # 23723-B2. [Note: For purposes of brevity, in all the following examples of pathogens, the corresponding wild-type phage will be indicated by the following phraseology: "Example of corresponding phage: ____".]
b) All the clinically important strains of *Klebsiella*, most notably *K. pneumoniae* [Example of corresponding phage: ATCC phage # 23356-B1].
c) All the clinically important strains of *Shigella*, most notably *S. dysenteriae* [Example of corresponding phage: ATCC phage # 11456a-B1].
d) All the clinically important strains of *Salmonella*, including *S. abortus-equi* [Example of corresponding phage: ATCC phage # 9842-B1], *S. typhi* [Example of corresponding phage: ATCC phage # 19937-B1], *S. typhimurium* [Example of corresponding phage: ATCC phage # 19585-B1], *S. newport* [Example of corresponding phage: ATCC phage # 27869-B1], *S. paratyphi*-A [Example of corresponding phage: ATCC phage # 12176-B1], *S. paratyphi*-B [Example of corresponding phage: ATCC phage # 19940-B1], *S. potsdam* [Example of corresponding phage: ATCC phage # 25957-B 2], and *S. pollurum* [Example of corresponding phage: ATCC phage # 19945-B1].
e) All the clinically important strains of *Serratia*, most notably *S. marcescens* [Example of corresponding phage: ATCC phage # 14764-B1].
f) All the clinically important strains of *Yersinia*, most notably *Y. pestis* [Example of corresponding phage: ATCC phage # 11953-B 1].
g) All the clinically important strains of *Enterobacter*, most notably *E. cloacae* [Example of corresponding phage: ATCC phage # 23355-B1].

2. All the clinically important *Enterococci*, most notably *E. faecalis* [Example of corresponding phage: ATCC phage # 19948-B 1] and *E. faecium* [Example of corresponding phage: ATCC phage #19953-B1].

3. All the clinically important *Haemophilus* strains, most notably *H. influenzae* [a corresponding phage is not available from ATCC for this pathogen, but several can be obtained from WHO or other labs that make them available publicly].

4. All the clinically important *Mycobacteria*, most notably *M. tuberculosis* [Example of corresponding phage: ATCC phage # 25618-B1], *M. avium-intracellulare, M. bovis*, and *M. leprae*. [Corresponding phage for these pathogens are available commercially from WHO, via The National Institute of Public Healthy & Environmental Protection, Bilthoven, The Netherlands].

5. *Neisseria gonorrhoeae* and *N. meningitidis* [corresponding phage for both can be obtained publicly from WHO or other sources].

6. All the clinically important *Pseudomonads*, most notably *P. aeuruginosa* [Example of corresponding phage: ATCC phage # 14203-B1].
7. All the clinically important *Staphylococci*, most notably *S. aureus* [Example of corresponding phage: ATCC phage # 27690-B 1] and *S. epidermidis* [corresponding phage are available publicly through the WHO, via the Colindale Institute in London].
8. All the clinically important *Streptococci*, most notably *S. pneumoniae* [Corresponding phage can be obtained publicly from WHO or other sources].
9. *Vibrio cholera* [Example of corresponding phage: ATCC phage # 14100-B1].

There are additional bacterial pathogens too numerous to mention that, while not currently in a state of antibiotic-resistance crisis, nevertheless make excellent candidates for treatment with anti-HDS physico-chemically altered bacteriophages that are able to delay inactivation by the HDS in accordance with the present invention. Thus, all bacterial infections caused by bacteria for which there is a corresponding phage can be treated using the present invention.

Any phage strain capable of doing direct or indirect harm to a bacteria is contemplated as useful in the present invention. Thus, phages that are lytic, phages that are lysogenic but can later become lytic, and nonlytic phages that can deliver a product that will be harmful to the bacteria are all useful in the present invention.

The animals to be treated by the methods of the present invention include but are not limited to man, his domestic pets, livestock, pisciculture, and the animals in zoos and aquatic parks (such as whales and dolphins).

The anti-HDS physico-chemically altered bacteriophages of the present invention can be used as a stand-alone therapy or as an adjunctive therapy for the treatment of bacterial infections. Numerous antimicrobial agents (including antibiotics and chemotherapeutic agents) are known in the art which would be useful in combination with anti-HDS physico-chemically altered bacteriophages for treating bacterial infections. Examples of suitable antimicrobial agents and the bacterial infections which can be treated with the specified antimicrobial agents are listed below. However, the present invention is not limited to the antimicrobial agents listed below, as one skilled in the art could easily determine other antimicrobial agents useful in combination with anti-HDS physico-chemically altered bacteriophage therapy.

| Pathogen | Antimicrobial or antimicrobial group |
|---|---|
| *E. coli* | |
| uncomplicated urinary tract infection | trimethoprim-sulfamethoxazole (abbrev. TMO-SMO), or ampicillin; 1st generation cephalosporins, ciprofloxacin |
| systemic infection | ampicillin, or a 3rd generation cephalsprorin; aminoglycosides, aztreonam, or a penicillin + a pencillinase inhibitor |
| *Klebsiella pneumoniae* | 1st generation cephalosporins; 3rd gener. cephalosporins, cefotaxime, moxalactam, amikacin, chloramphenicol |
| Shigella (various) | ciprofloxacin; TMO-SMO, ampicillin, chloramphenicol |
| Salmonella: | |
| *S. typhi* | chloramphenicol; ampicillin, TMO-SMO |
| non-*typhi* species | ampicillin; chloramphenicol, TMO-SMO, ciprofloxacin |

-continued

| Pathogen | Antimicrobial or antimicrobial group |
|---|---|
| *Yersinia pestis* | streptomycin; tetracycline, chloramphenicol |
| *Enterobacter cloacae* | 3rd generation cephalosporins, gentamicin, or tobramycin; carbenicillin, amikacin, aztreonam, imipenem |
| Hemophilus influenzae: | |
| meningitis | chloramphenicol or 3rd generation cephalosporins; ampicillin |
| other H. infl. infections | ampicillin; TMO-SMO, cefaclor, cefuroxime, ciprofloxacin |
| *Mycobacterium tuberculosis* and *M. avium-intracellulare* | isoniazid (INH) + rifampin or rifabutin, the above given along with pyrazinamide +/or ethambutol |
| Neisseria: | |
| *N. meningitidis* | penicillin G; chloramphenicol, or a sulfonamide |
| *N. gonorrhoeae*: | |
| penicillin-sensitive | penicillin G; spectinomycin, ceftriaxone |
| penicillin-resistant | ceftriaxone; spectinomycin, cefuroxime or cefoxitin, ciprofloxacin |
| *Pseudomonas aeruginosa* | tobramycin or gentamycin (+/− carbenicillin, aminoglycosides); amikacin, ceftazidime, aztreonam, imipenem |
| Staph *aureus* | |
| non-penicillinase producing | penicillin G; 1st generation cephalosporins, vancomycin, imipenem, erythromycin |
| penicillinase producing | a penicillinase-resisting penicillin; 1st generation cephalosporins, vancomycin, imipenem, erythromycin |
| *Streptococcus pneumoniae* | penicillin G; 1st gener. cephalosporins, erythromycin, chloramphenicol |
| *Vibrio cholera* | tetracycline; TMO-SMO |

The routes of administration include but are not limited to: oral, aerosol or other device for delivery to the lungs, nasal spray, intravenous, intramuscular, intraperitoneal, intrathecal, vaginal, rectal, topical, lumbar puncture, intrathecal, and direct application to the brain and/or meninges. Excipients which can be used as a vehicle for the delivery of the phage will be apparent to those skilled in the art. For example, the physico-chemically altered phage could be in lyophilized form and be dissolved just prior to administration by IV injection. The dosage of administration is contemplated to be in the range of about $10^6$ to about $10^{13}$ pfu/per kg/per day, and preferably about $10^{12}$ pfu/per kg/per day. The phage are administered until sufficient elimination of the pathogenic bacteria is achieved.

With respect to the aerosol administration to the lungs, the anti-HDS physico-chemically altered phages are incorporated into an aerosol formulation specifically designed for administration to the lungs by inhalation. Many such aerosols are known in the art, and the present invention is not limited to any particular formulation. An example of such an aerosol is the Proventil™ inhaler manufactured by Schering-Plough, the propellant of which contains trichloromonofluoromethane, dichlorodifluoromethane and oleic acid. The concentrations of the propellant ingredients and emulsifiers are adjusted if necessary based on the phage being used in the treatment. The number of phages to be administered per aerosol treatment will be in the range of $10^6$ to $10^{13}$ pfu, and preferably $10^{12}$ pfu.

For wild-type phage that have not been genotypically modified to delay inactivation by the HDS, physico-chemical alteration will provide a means for such phage to delay that inactivation. For phage that have been genotypically modified to delay inactivation by the HDS, physico-chemical alteration will provide an additional and synergistic measure of protection against such HDS inactivation. Furthermore, for both the genotypically-modified and the wild-type phage, physico-chemical alteration will shield the phages from immune cells and complement, minimizing the rate of antibody formation against the phage antigens.

In summary, the use of physico-chemically altered bacteriophage to delay inactivation by the HDS provides the following advantages: 1) it enables the use of smaller whole body dosages of phage than would be required with non-modified phage; 2) because of the overall lower whole body dosages required, and the fact that the phage are sheltered from the HDS, there is a delay and a minimization of antibody-antigen interactions, so that 3) the physico-chemical alteration prolongs the number of weeks or months that phage therapy may remain effective in a given animal, and increases the number of courses of phage therapy that may usefully be given over time.

The foregoing embodiments of the present invention are further described in the following Examples. However, the present invention is not limited by the Examples, and variations will be apparent to those skilled in the art without departing from the scope of the present invention. In particular, any bacteria and phage known to infect said bacteria can be substituted in the experiments of the following examples.

EXAMPLES

Example 1

PEGylating Bacteriophage to Block their Antigenic Sites from Interaction with the Host Defense System Part 1. Protecting the Tail Portion of the Phage from PEGylation:

Tails of a lambda coliphage are isolated by sonication and centrifugation. The tail particles resulting from sonication are injected into rabbits to raise antibodies to the tail proteins, following procedures known in the art. The anti-tail antibodies are then immobilized on a solid support column using CNBR-activated sepharose 4B (Pharmacia, Piscataway, N.J.). An excess number of whole, intact lambda phage are incubated with the column-immobilized anti-tail antibodies, to allow the formation of complexes between the tail antigens of the intact phage and the anti-tail antibodies immobilized on the support column. The formation of these complexes immobilizes the intact phage by their tail portions only, leaving all non-tail proteins exposed to the PEGylation reagents. Free phage that have not been immobilized are eluted with normal saline, and discarded.

Part 2. PEGylation of the Phage:

Step 1. Preparation of the PEG Derivative:

The PEG derivative used is monomethoxypoly(ethylene glycol), abbreviated "mPEG". The mPEG is activated with succinimidyl carbonate, by methods known in the art [See e.g. Zalipsky et. al., Use of functionalized polyethylene glycols for modification of poly-peptides, in press.] In this method, mPEG, of molecular weight 5000 (Union Carbide, 60 g, 12 mmol), dried by azeotropic removal of toluene, is dissolved in toluene/dichloromethane (3:1, 200 ml) and treated under a well-ventilated hood with a toluene solution of phosgene (30 ml, 57 mmol) overnight. The solution is evaporated to dryness and the remainder of the phosgene is removed under vacuum, under the hood. The residue is redissolved in toluene/dichloromethane (2:1, 150 ml) and treated with solid N-hydroxysuccinimide (2.1 g, 18 mmol) followed by triethylamine (1.7 ml, 12 mmol). After 3 hours the solution is filtered and evaporated to dryness. The residue is dissolved in warm (50° C.) ethyl acetate (600 ml) and trace insolubles are filtered out. The residue is cooled to facilitate precipitation of the polymer. The product is collected by filtration and then recrystallized once more from ethyl acetate. The product is dried in vacuo over $P_2O_5$. The resulting product is methoxypoly(ethylene glycol)-N-succinimidyl carbonate ("SC-PEG").

Step 2. Altering the Phage Proteins Using SC-PEG:

SC-PEG is mixed into a quantity of 0.1 M sodium phosphate (pH 7.8) sufficient to completely fill the column of immobilized phages and to achieve a concentration of 0.033 mmol SC-PEG per ml of sodium phosphate. The column is filled completely with the mixture, adding sodium hydroxide (0.5 N) as needed to maintain pH 7.8 for the duration of the reaction, which is terminated at 30 min. The excess of free SC-PEG is removed by diafiltration using 50 mM phosphate buffered saline. The altered phage are separated from the column-bound anti-tail antibodies by eluting with glycine buffer at pH 2.6, then immediately neutralizing to pH 7.5 with TRIS base.

Part 3. Determining the Extent of PEGylation of the Phage Proteins:

The number of amino groups of the phage proteins that have reacted with SC-PEG is measured using the trinitrobenzenesulfonate (TNBS) assay, [See e.g. Habeeb, A. *Anal. Biochem.* 1966, 14, 328]

Example 2

Demonstration that PEGylated Phage Remain Lytic in Vitro

A 100 cc broth containing the host strain of coliphage (in a concentration of $1 \times 10^{12}$ bacteria/cc) is inoculated with $1 \times 10^{12}$ PEGylated phage suspended in 1 cc of sterile normal saline. A control broth of the same bacteria is inoculated in the same way, with the unmodified coliphage. The determination that both the modified and the unmodified phage lyse their respective broths in roughly equal periods of time is shown by:

a) roughly equal turbidimetric measures in both broths;

b) sterility in both broths, evidenced by no bacterial growth on agar, from plating out of both lysed broths; and c) pfu experiments showing that both cleared broths have concentrations of daughter phage at least 1000 times higher than the concentrations of phage in the broths at time zero.

Example 3

Demonstration that PEGylated Phage Take Longer to be Inactivated by the HDS as Compared to Unmodified Phage Two groups of mice are injected with phage as specified below:

Group 1: The experimental group receives an IV injection consisting of $1 \times 10^{12}$ of the PEGylated phage, suspended in 0.5 cc of sterile normal saline.

Group 2: The control group receives an IV injection consisting of $1\times10^{12}$ of the unmodified phage from which the modified phage were derived, suspended in 0.5 cc of sterile normal saline.

Both groups of mice are bled at regular intervals, and the blood samples are assayed for phage content (by pfu assays) to determine the following:

1) Assays for half-life of the two phages: For each group of mice, the point in time is noted at which there remains in circulation only half (i.e., $1\times10^6$) the amount of phage administered at the outset.

2) Assays for absolute numbers: For each group of mice, a sample of blood is taken at precisely 1 hour after administration of the phage.

Example 4

Demonstration that PEGylated Phage Remain Lytic In VIVO, and Have a Better Ability than Unmodified Phage to Prevent a Lethal Infection Part 1. Peritonitis Model:

An $LD_{50}$ dosage of *E. coli* is administered intraperitonally (IP) to laboratory mice. The strain of *E. coli* used is one known to be lysed by the coliphage strain that has been PEGylated. The treatment modality is administered precisely 20 minutes after the bacteria are injected, but before the onset of symptoms. The treatment modalities consist of the following:

Group 1: The experimental group receives an IP injection consisting of $1\times10^{12}$ of the PEGylated lambda coliphage, suspended in 2 cc of sterile normal saline.

Group 2: A first control group receives an IP injection consisting of $1\times10^{12}$ of the unmodified phage, suspended in 2 cc of normal sterile saline.

Group 3: A second control group receives an IP injection of sterile normal saline.

The following criteria are measured to determine the effectiveness of the PEGylated phage.

(1) Survival of the animals: Survival rates of the mice receiving the PEGylated phage are compared to the survival rates of the mice receiving the unmodified phage.

(2) Bacterial counts: Samples of peritoneal fluid are withdrawn every ½ hour from the three groups of infected mice, and are streaked on culture dishes. The rate of decrease in *E. coli* colony counts in the three groups is compared.

(3) Phage counts: Samples of peritoneal fluid from the different groups of mice are compared in plaque forming unit experiments.

Part 2. Bacteremia Model:

An $LD_{50}$ dosage of *E. coli* is administered intravenously (IV) to laboratory mice, where the strain of *E. coli* used is known to be lysed by the coliphage strain that was PEGylated. The treatment modality (see below) is administered precisely 20 minutes after the bacteria are injected, but before the onset of symptoms. All groups are bled on an hourly basis. The treatment modalities consist of the following:

Group 1: The experimental group receives an IV injection consisting of $1\times10^{12}$ of the PEGylated lambda coliphage, suspended in 0.5 cc of sterile normal saline.

Group 2: A first control group receives an IV injection consisting of $1\times10^{12}$ of the unmodified phage, suspended in 0.5 cc of sterile normal saline.

Group 3: A second control group receives an IV injection of 0.5 cc of sterile normal saline.

The following criteria are measured to determine the effectiveness of the PEGylated phage.

(1) Survival of the animals: Survival rates of the mice receiving the PEGylated phage are compared to the survival rates of the mice receiving the unmodified phage.

(2) Bacterial counts: The serial blood samples are streaked on culture dishes. The rate of decrease in *E. coli* colony counts in the three groups is compared.

(3) Phage counts: The serial blood samples are tested in plaque forming unit experiments. The number of plaque forming units in the three groups is compared.

We claim:

1. A PEGylated bacteriophage.

2. The bacteriophage according to claim 1, wherein said phage is specific for bacterial families selected from the group consisting of *Escherichia, Klebsiella, Shigella, Salmonella, Serratia, Yersinia, Enterobacter, Enterococci, Haemophilus, Mycobacteria, Neisseria, Pseudomonas, Staphylococci, Streptococci* and *Vibrio*.

* * * * *

UNITED STATES PATENT AND TRADEMARK OFFICE
CERTIFICATE OF CORRECTION

PATENT NO. : 7,332,307 B2  Page 1 of 1
APPLICATION NO. : 10/659698
DATED : February 19, 2008
INVENTOR(S) : Carlton et al.

It is certified that error appears in the above-identified patent and that said Letters Patent is hereby corrected as shown below:

On the Title page item (56), column 2, line 13 OTHER PUBLICATIONS, delete "agains" and insert -- against --, therefor.

On the Title page item (56), column 2, lines 16-18 OTHER PUBLICATIONS, below "4541.*" delete "O'Riordan CR et al...(May 20, 1990)*".

At page 1, column 2, line 19 of the section entitled OTHER PUBLICATIONS, delete "Bacteiophage" and insert -- Bacteriophage --, therefor.
At page 2, column 2, line 26 of the section entitled OTHER PUBLICATIONS, delete "bacteriphages,"" and insert -- bacteriophages," --, therefor.
Column 9, line 6, delete "B 1]" and insert -- B1] --, therefor.
Column 9, line 6, delete "[corresponding" and insert -- [Corresponding --, therefor.
Column 12, line 35 (approx.), after "328]" insert -- . --.

Signed and Sealed this

Sixteenth Day of September, 2008

JON W. DUDAS
*Director of the United States Patent and Trademark Office*